(12) United States Patent
Cook

(10) Patent No.: US 8,753,358 B2
(45) Date of Patent: Jun. 17, 2014

(54) DIAL FAN HERNIA MESH SYSTEM

(76) Inventor: Douglas Wesley Cook, Exeter, CA (US)

( * ) Notice: Subject to any disclaimer, the term of this patent is extended or adjusted under 35 U.S.C. 154(b) by 590 days.

(21) Appl. No.: 12/690,892

(22) Filed: Jan. 20, 2010

(65) Prior Publication Data
US 2011/0178538 A1 Jul. 21, 2011

(51) Int. Cl.
*A61B 17/00* (2006.01)
(52) U.S. Cl.
USPC ........... 606/151; 606/190; 600/210; 600/214; 600/215
(58) Field of Classification Search
None
See application file for complete search history.

(56) References Cited

U.S. PATENT DOCUMENTS

| | | | | |
|---|---|---|---|---|
| 2,142,080 | A * | 1/1939 | Asplund | 416/69 |
| 5,258,000 | A * | 11/1993 | Gianturco | 606/151 |
| 5,267,554 | A * | 12/1993 | Wilk | 600/224 |
| 5,395,383 | A * | 3/1995 | Adams et al. | 606/151 |
| 5,634,931 | A | 6/1997 | Kugel | |
| 5,769,864 | A | 6/1998 | Kugel | |
| 5,824,082 | A | 10/1998 | Brown | |
| 5,916,225 | A | 6/1999 | Kugel | |
| 6,120,539 | A | 9/2000 | Eldridge et al. | |
| 6,171,318 | B1 | 1/2001 | Kugel et al. | |
| 6,174,320 | B1 | 1/2001 | Kugel et al. | |
| 6,176,863 | B1 | 1/2001 | Kugel et al. | |
| 6,224,616 | B1 | 5/2001 | Kugel | |
| 6,280,453 | B1 | 8/2001 | Kugel et al. | |
| 6,290,708 | B1 | 9/2001 | Kugel et al. | |
| 7,625,392 | B2 * | 12/2009 | Coleman et al. | 606/213 |
| 8,052,759 | B2 * | 11/2011 | Dupic et al. | 623/23.72 |
| 8,252,022 | B2 * | 8/2012 | Holman et al. | 606/213 |
| 2004/0073257 | A1 * | 4/2004 | Spitz | 606/220 |
| 2004/0204694 | A1 * | 10/2004 | Nicholson | 604/327 |
| 2007/0066980 | A1 * | 3/2007 | Leahy | 606/151 |

(Continued)

FOREIGN PATENT DOCUMENTS

| | | |
|---|---|---|
| EP | 0 543 499 A1 | 5/1993 |
| WO | WO 2007/087146 | 8/2007 |
| WO | WO 2007/133811 | 11/2007 |

OTHER PUBLICATIONS

PCT Notification of Transmittal of The International Search Report and the Written Opinion of the International Searching Authority or The Declaration for PCT Counterpart Application No. PCT/US2011/021754 Containing International Search Report, 14 pgs. (Mar. 17, 2011).

(Continued)

*Primary Examiner* — Melanie Tyson
*Assistant Examiner* — Todd J Scherbel
(74) *Attorney, Agent, or Firm* — Blakely, Sokoloff, Taylor & Zafman LLP

(57) ABSTRACT

Hernia repair using a mesh patch and a placement tool is described. The placement tool includes a plurality of adjustable blades and a control to move the adjustable blades between a clustered position that allows the blades to be inserted in an opening in a ply of the mesh patch and an expanded position to spread the mesh patch out in a planar fashion. Repair of a hernia includes compressing the mesh patch, inserting the adjustable blades of a placement tool into the opening in the mesh patch, inserting the mesh patch and tool into a patient, moving the adjustable blades from the clustered position to the expanded position, affixing the mesh patch to the patient, moving the adjustable blades from the expanded position to the clustered position, and removing the placement tool from the mesh patch and the patient.

12 Claims, 4 Drawing Sheets

(56) References Cited

U.S. PATENT DOCUMENTS

| | | | | |
|---|---|---|---|---|
| 2007/0185506 | A1* | 8/2007 | Jackson | 606/151 |
| 2009/0326676 | A1 | 12/2009 | Dupic et al. | |
| 2010/0241145 | A1* | 9/2010 | Cook | 606/151 |
| 2011/0040311 | A1* | 2/2011 | Levin et al. | 606/151 |
| 2011/0224704 | A1* | 9/2011 | Bailly et al. | 606/151 |
| 2011/0295283 | A1* | 12/2011 | Darois et al. | 606/151 |

OTHER PUBLICATIONS

Hernia Repair, Bard* Ventralex* Hernia Patch, Technique Guide, Open Ventral Hernia Repair and Laparoscopic Trocar Site Closure, Davol Inc. (a Bard Company), http://www.davol.com/Davol/content/ventralex.aspx, 16 pages, downloaded on Feb. 16, 2009.

"MMDI's Rebound HRD Recognized as a '2006 Innovation of the Year' by the Society of Laparoendoscopic Surgeons", Minneapolis MN, Sep. 27, 2006, 1 page.

"NProduct Spotlight: An Innovation in Hernia Repair", MMDI Minnesota Medical Development, Inc., http://www.2mdinc.com/, Copyright 2006, downloaded on Nov. 11, 2009 1 page.

"Simplify Ventral Hernia Repair Using the Rebound HRD V", For Laparoscopic or Open Ventral Repair, Rebound HRD V, http://www.2mdinc.com/Products/products2.html, downloaded on Nov. 11, 2009, 1 page.

"Simplify Ventral Hernia Repair Using the Rebound HRD V", MMDI Minnesota Medical Development, Inc., Plymouth MN, http://www.2mdinc.com, downloaded on Nov. 11, 2009, 2 pages.

* cited by examiner

DIAL FAN HERNIA MESH SYSTEM

FIELD

Embodiments of the present invention relate generally to the field of surgical repair of abdominal wall hernias using a mesh patch.

BACKGROUND

Repair of hernias, most commonly in the abdominal wall, is one of the most frequent surgeries performed today. Surgically implantable mesh patches are often used for the repair of these hernias and intended for permanent placement within a patient's body space. A mesh patch is implanted in the patient to provide structural strength and minimize the chance of hernia recurrence. An example of such a hernia mesh patch is described in U.S. Pat. No. 6,120,539 of Eldridge et al.

Hernia repair utilizing mesh patches, however, typically presents at least the following difficulties. First, mesh patches typically do not have enough memory in the mesh material to easily return to a planar position once the mesh patch is inserted within the abdominal cavity. This makes accurate placement of the mesh patch difficult, as it will not easily hold its shape once inserted. Second, mesh patches typically lack points to secure sutures or other protection that would keep the surgeon from injuring anatomical features under the mesh during fixation. This aggravates the problems in accurately and evenly placing the mesh. Third, once a mesh patch is inserted into a patient, it can be difficult to manipulate, place, and hold the mesh patch in the correct position over the tissue being repaired. These issues encountered during the installation of patches may lead to non-uniform and unequal attachment of the patch to the abdominal wall around the hernia, which subsequently may lead to complications for the patient and, in some cases, may be life-threatening.

Modifications have been made to the mesh hernia patches in an attempt to address these issues. For example, a mesh with a "memory ring" has been developed to address the first issue. The memory ring is a mono-filament that is contained in the perimeter of the patch. The mono-filament has sufficient spring tension and memory to keep the mesh planar once in place. This memory ring, however, is bulky and sometimes does not work well. Further, it leads to additional foreign material being placed in the patient, which may also lead to medical complications.

SUMMARY

A method and apparatus are described for the repair of abdominal wall hernias. An adjustable fan mesh patch system is described. For one embodiment, the placement tool includes a plurality of adjustable fan blades and a control to move the adjustable blades between a clustered position that allows the blades to be inserted in an opening in a ply of the mesh patch and an expanded position to spread the mesh patch out in a planar fashion. For one embodiment, repair of a hernia includes inserting the adjustable blades of a placement tool into the opening in the mesh patch, compressing the mesh patch, inserting the mesh patch and tool into a patient, moving the adjustable blades from the clustered position to the expanded position, affixing the mesh patch to the patient, moving the adjustable blades from the expanded position to the clustered position, and removing the placement tool from the mesh patch and the patient.

Other features and advantages of embodiments of the present invention will be apparent from the accompanying drawings and from the detailed description that follows.

BRIEF DESCRIPTION OF THE DRAWINGS

Embodiments of the present invention are illustrated by way of example and not limitation in the figures of the accompanying drawings, in which like references indicate similar elements, and in which.

DETAILED DESCRIPTION

A method and apparatus are described for repairing abdominal hernias that provide for faster, more accurate insertion of a mesh patch and a reduction in patient complications. For one embodiment, the placement tool includes a plurality of adjustable blades and a control to move the adjustable blades between a clustered position that allows the blades to be inserted in an opening in a ply of the mesh patch and an expanded position to spread the mesh patch out in a planar fashion.

Figure 1:
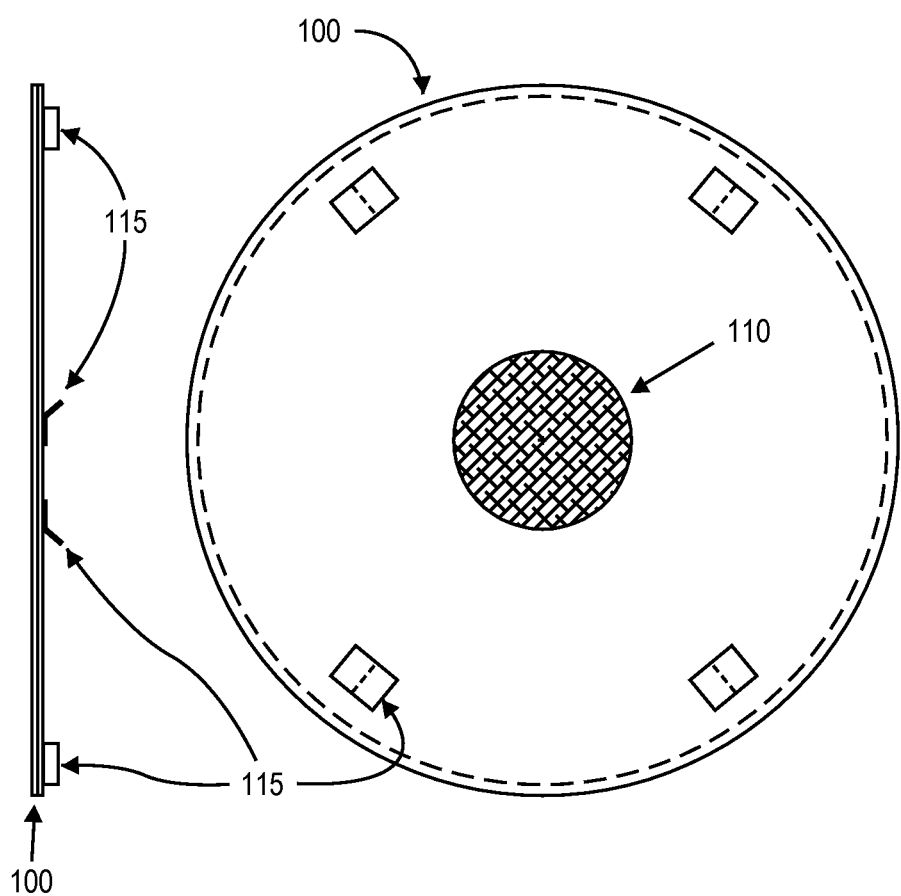
FIG. 1 shows a top view and a side view of a hernia mesh patch according to one embodiment.

FIG. 1 illustrates a top view and a side view of a circular hernia repair mesh patch 100 according to an embodiment of the invention. The mesh patch 100 is made of a porous, lightweight, permeable material, which is known in the medical industry. The mesh patch 100 includes two layers of the material. For one embodiment, the top ply and bottom ply are stitched, or otherwise affixed, to one another at their respective perimeters. For one embodiment the mesh patch 100 is circular. For example, one embodiment of the mesh patch 100 is a circle with diameter of approximately four inches. Alternatively, the mesh patch 100 can be square, rectangular, oval, or other similar shape.

The mesh patch 100 includes an opening 110 in the top ply of material. For one embodiment, the opening 110 is circular and near the center of the mesh patch 100. For example, one embodiment of the opening 110 is a circle with a diameter of approximately one inch. Alternatively, the opening 110 can be square, rectangular, oval, triangular, a slit, a shape similar to that of a placement tool's blades, or other similar shape that will allow for the insertion of the placement tool's blades (described below). For one embodiment, the top ply of material surrounding the opening 110 includes reinforcement, such as additional stitching, to strengthen the top ply of material when the placement tool's blades are inserted in or removed from the mesh patch 100.

For one embodiment, a surgeon affixes the mesh patch 100 to a patient by suturing the top ply of the mesh patch 100. Alternatively, one or more suture tabs 115 are affixed to the top of the mesh patch 100. The suture tabs 115 provide points by which the surgeon can affix the mesh patch 100 to the patient. The suturing of the suture tabs 115 anchors the mesh patch 100 while the patient recovers. For one embodiment, both the suture tabs 115 and the sutures themselves are made of materials that dissolve in situ within a period of time (e.g., a plurality of months). As illustrated in the side view of the mesh patch 100, a portion of each suture tab 115 is fixed to the planar surface of the mesh patch 100 and an unfixed portion of each suture tab 115 is folded upward to be available for affixing to the patient with a suture. As a result, the surgeon can suture the tab 115 to the patient without having to drive the suture through the bottom of the mesh. This helps avoid unintended punctures and associated problems.

Figure 2:
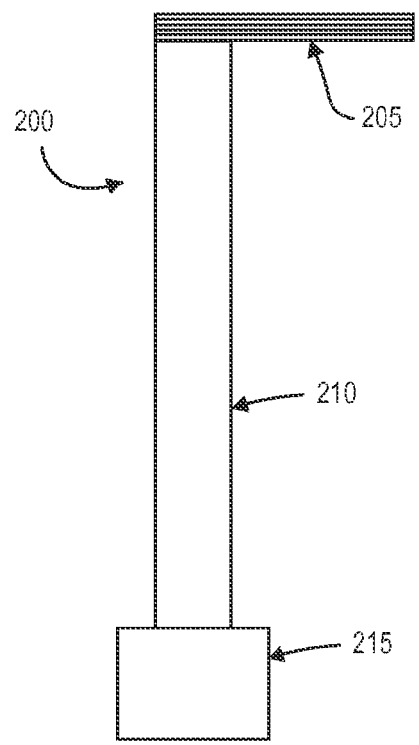
FIG. 2 shows a side view of an exemplary hernia mesh patch placement tool with its adjustable blades in a clustered position.

FIG. 2 shows a side view of an exemplary hernia mesh patch placement tool 200 with its adjustable protrusions 205 in a clustered position. Embodiments described herein refer to the protrusions 205 as "fan blades" or simply as "blades" due to the similarity of the exemplary illustration of the protrusions to the blades of a fan. The use of the term blades, however, is not intended to be limiting and, for some embodiments, the protrusions 205 have shapes other than that of fan blades.

For one embodiment, the placement tool 200, or any component of placement tool 200, is made of metal (e.g., 300 series surgical grade stainless steel), nylon, plastic, etc., or a combination thereof. For one embodiment, the placement tool 200 is constructed so as to be disposable. Alternatively, the placement tool 200 is constructed so as to withstand multiple uses and heated sterilizations—e.g., in an autoclave.

A plurality of adjustable blades 205 are located at or near a distal end of the placement tool 200 (the distal end being the end of the tool to be inserted first into a patient and, therefore, distal with respect to the operator of the tool). The blades are shown in a clustered position in FIG. 2. For one embodiment, the blades 205 are arranged to stack one on top of another in the clustered position (as shown). Alternatively, the blades 205 are arranged to be side-by-side or a combination of side-by-side and stacked upon one another when in the clustered position (not shown). For yet another embodiment, the clustered position of the blades 205 refers to a position wherein the blades 205 are in any position such that they may be inserted into an opening 110 in a mesh patch and is not limited to the blades overlapping or being positioned side-by-side. For example, the clustered position can refer to the blades 205 as being retracted, at least partially, within the elongated handle 210. Alternatively, the blades 205 themselves could be retracted and expanded in a telescopic manner and the clustered position of blades 205 could refer to telescopic blades in a retracted position. For yet another embodiment, the clustered position of the blades 205 could refer to a combination of one or more of the embodiments above.

For one embodiment, the blades 205 are each between one and two inches in length (e.g., the direction illustrated as perpendicular to the elongated handle 210) and between $1/100$ and $1/10$ inches in height (the direction in which the blades 205 are stacked). Additionally, the blades 205 are substantially perpendicular to the elongated handle—e.g., within 10 degrees of perpendicular. Alternatively, for an embodiment in which the blades 205 retract within the elongated handle 210, portions of the blades 210 that are retracted within the handle would be substantially parallel to the elongated handle—e.g., within 10 degrees of parallel and with a curved path to allow for the blades to expand outwards from the elongated handle in a substantially perpendicular manner.

The elongated handle 210 allows a user of the placement tool 200 to manipulate the device with some distance between the hand of the user and the blades 205. As a result, the is some distance between the hand of the user and the mesh patch 100 once the blades 205 are inserted into the opening 110 of the mesh patch 100. For one embodiment, the elongated handle 210 is cylindrical in shape and between four and eight inches in length (from the proximal end to the distal end). Alternatively, the elongated handle 210 would have another shape (e.g., having a cross-section in the shape of an octagon) that would allow for the adjustment of the blades 205 described herein.

Figure 4:
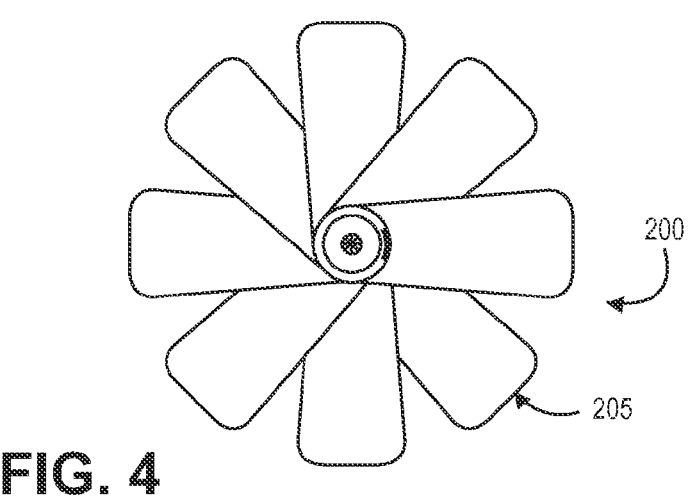
FIG. 4 shows a top view of an exemplary hernia mesh patch placement tool with its adjustable blades in an expanded position.

The control 215 is located at or near a proximal end of the elongated handle 210 (again, proximal with respect to the operator of the tool). While embodiments described herein are collectively referred to as a "Dial Fan" hernia mesh system, embodiments of the control 215 are not limited to the use of a dial. For some embodiments, the control 215 is a rod, knob, crank, handle, dial, switch, plunger, etc. that enables a user to adjust the position of the blades 205. For example, the user rotates or otherwise moves the control in one direction to cause the blades 205 to spread out into an expanded position (e.g., in a configuration similar to a ceiling fan, as shown in FIG. 4) and rotates the control in the opposite direction to cause the blades 205 to return to a clustered position. As described above, describing the blades 205 in a clustered position includes retracted them in a telescopic fashion or within the elongated handle 210. Accordingly, the expanded position would include expanding the blades telescopically or otherwise causing the blades to expand outward from the elongated handle 210.

The control 215 is connected to the blades 205 to control the movement of the blades 205. For example, manipulation of control 215 may be translated to the blades 205 via a rotatable or plunger-type shaft that is located within the elongated handle 210.

For one embodiment, the control 215 is cylindrical in shape and wider than the elongated handle 210 (as shown) for ease of manipulation. For example, for one embodiment, the elongated handle 210 is approximately one half inch wide (i.e., if a cylinder, the diameter of the cylinder) while the control 215 is approximately one inch wide (i.e., again, if a cylinder, the diameter of the cylinder). Alternatively, the control 215 is as wide as or less wide than the elongated handle 210.

Figure 3:
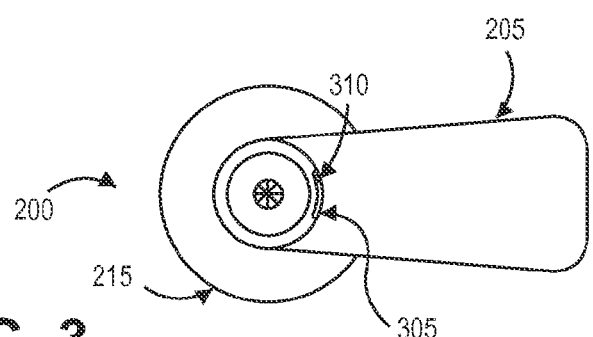
FIG. 3 shows a top view of an exemplary hernia mesh patch placement tool with its adjustable blades in a clustered position.

FIG. 3 shows a top view of an exemplary hernia mesh patch placement tool 200 with its adjustable blades 205 in a clustered position. Similar to the exemplary illustration in FIG. 2, the blades 205 are stacked one on top of the next so that only the top blade 205 is visible from the top view. Additionally, similar to the exemplary illustration in FIG. 2, the control 215 has a wider diameter than the elongated handle 210 and, therefore, is visible from the top view.

For one embodiment, each blade 205 includes a slot 305 to receive a raised feature 310 from the blade 205 beneath it. For one embodiment, the bottom blade optionally does not include a slot 305 and the top blade does not include a raised feature 310. Accordingly, as one blade is caused to rotate, the slot 305 will allow some rotational distance between it and the next blade (above or below) before the raised feature 310 reaches an end of the slot 305 and causes the next blade to rotate as well. For example, if the blades 205 are all in the clustered position shown in FIG. 2, rotation of the control 215 will cause the bottom blade to rotate and the raised feature 310 of the bottom blade will travel along the slot 305 of the blade immediately above the bottom blade. Once the raised feature 310 of the bottom blade reaches the end of the slot 305 of the next blade, the continued rotation will cause both blades to rotate. In turn, the raised feature 310 of the second to the bottom blade will then begin to travel along the slot 305 of the third blade. This will continue until the blades have rotated into an expanded position. The slots 305 and raised features 310 will function in a similar fashion when the control 215 is rotated in the opposite direction and cause the blades to return to a clustered position.

Alternatively, the blades 205 may be connected in another fashion or each blade may have its own connection to the control 215 or rotating shaft. For example, the use of the raised feature and slot combination, or an equivalent, may be implemented internally within the elongated handle 210 via gearing or another means so as not to require the blades themselves to overlap.

FIG. 4 shows a top view of an exemplary hernia mesh patch placement tool 200 with the adjustable blades 205 in an expanded position. The adjustable blades 205 assist in the placement and manipulation of a mesh patch 100 during surgery. In the clustered position, the placement tool 200 is compact for a less invasive insertion into a patient. Once inserted, the expanded position of the blades 205 stretches the mesh patch 100 into a substantially planar shape and allows the surgeon to easily manipulate the position of the mesh patch 100.

For one embodiment, the blades 205 partially overlap one another in the expanded position, but still have some space between their ends (as shown in FIG. 4). Alternatively, the blades 205 have no overlap—i.e., space between the entirety of each blade, or the blades 205 are shaped or positioned such that no space exists between the blades 205 in an expanded position. For one embodiment, each blade is approximately one half to three quarters of an inch in width. The length of the blades 205 is similar to the length of the blades 205 as described above (length refers to the dimension of the blades 205 extending radially outward from the elongated handle 210). The number of the blades 205 on the placement tool 200 may vary depending upon the size of the mesh patch 100, the width of each blade 205, and the gaps between each blade. For one embodiment, the placement tool has between 4 and 8 blades. Additionally, the size (e.g., width/length) of each blade 205 may vary depending on the corresponding shape of the mesh patch 100. For example, if the mesh patch 100 is in the shape of an oval, some of the blades 205 could be longer to match the long axis of the oval while other blades 205 could be shorter to match the short axis of the oval.

When the placement tool 200 is used to position a mesh patch 100, the expanded blades 205 provide a barrier between the top ply of the mesh patch 100 to be sutured and viscera beneath the hernia defect. This barrier helps prevent the unintentional puncture of the viscera when suturing the mesh patch 100 to the patient. The number, width, and overlap of the blades each will affect the amount of protection the placement tool provides while the surgeon sutures the top ply to the patient.

Figure 5:
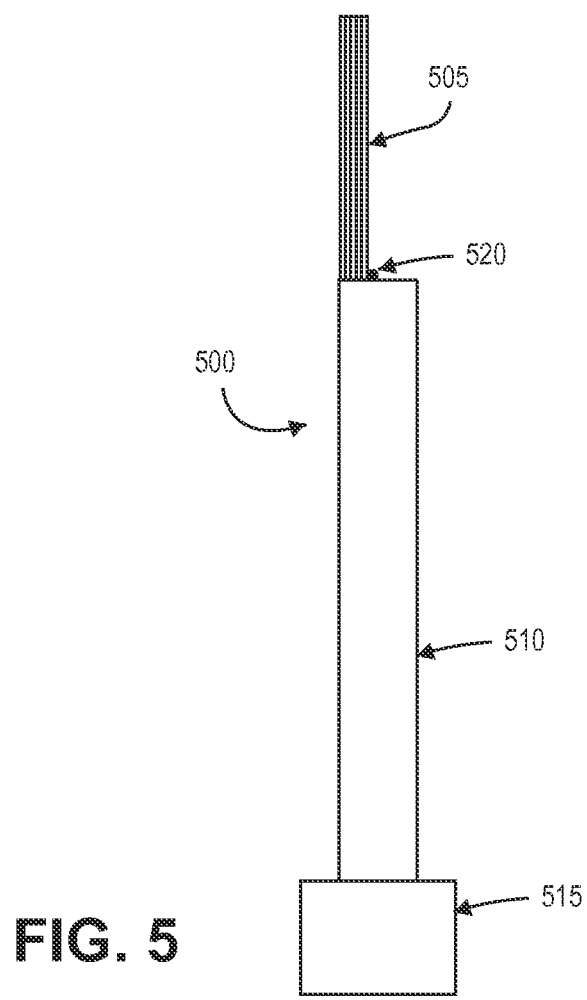
FIG. 5 shows a side view of an exemplary hernia mesh patch placement tool with articulating adjustable blades in a clustered position.

FIG. 5 shows a side view of an exemplary hernia mesh patch placement tool 500 with articulating blades 505 in a clustered position. The placement tool 500 is similar to the placement tool 200 described above—i.e., blades 505, elongated handle 510, and control 515 are all similar to blades 205, elongated handle 210, and control 215 described with reference to FIGS. 2-4. Articulating blades 505, however, allow the blades to move between a position that is substantially perpendicular to the elongated handle 510 (as described above) and substantially parallel to the elongated handle 510—e.g., within 10 degrees of parallel. Articulating blades 505 provide for additional maneuverability of the placement tool within a confined space.

For one embodiment, the articulation of the blades 505 is enabled by a hinge 520 located between the blades 505 and the distal end of the elongated handle 510. The articulating blades 505 are disconnected from the control 515 when in a position that is substantially parallel to the elongated handle 510 and connected to the control 515 when in a position that is substantially perpendicular to the elongated handle 510.

Figure 6:
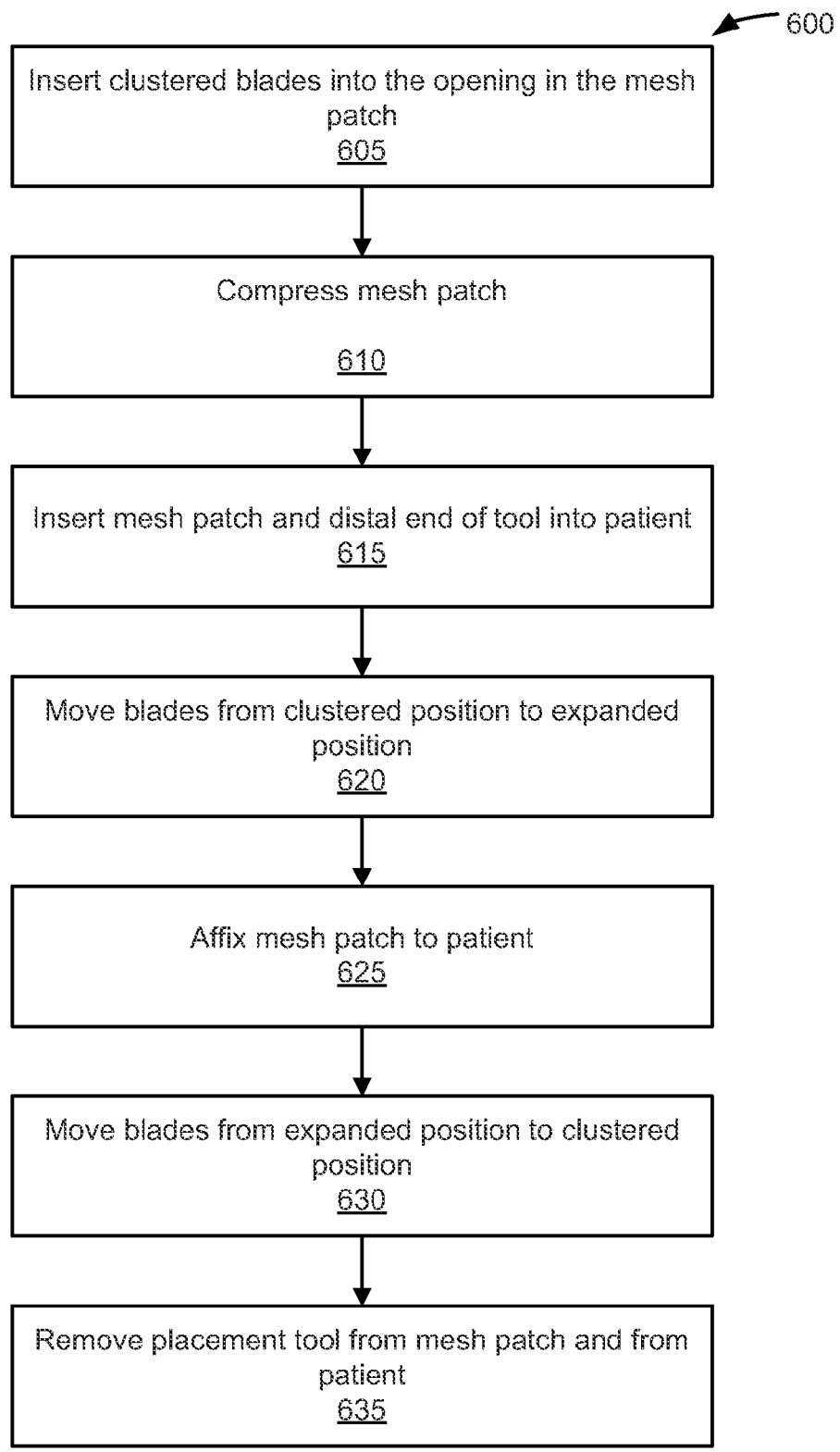
FIG. 6 is a flow chart of an exemplary method of repairing a hernia utilizing an adjustable fan hernia mesh patch system according to an embodiment of the invention.

FIG. 6 is a flow chart of an exemplary method 600 of repairing a hernia with a mesh patch 100 in combination with a placement tool 200, as described above with reference to FIGS. 1-5. At block 605, after dissecting an opening in the patient, the surgeon inserts the clustered blades 205 into the opening 110 in the mesh patch 100. At block 610, the surgeon prepares the mesh patch 100 for insertion by folding or otherwise compressing the mesh patch 100 around the clustered blades 205. At block 615, once the mesh patch 100 has been thus compressed in size, the surgeon inserts the mesh patch 100 and distal end of the placement tool 200 into the patient.

At block 620, the surgeon then decompresses the mesh patch 100 by operating control 215 to move the blades 205 from their clustered position to an expanded position and, therefore, to spread the mesh patch 100 out in a planar fashion. If the blades 505 are articulating, the surgeon will first move the clustered blades 505 to a position that is substantially perpendicular with the elongated handle 510 prior to moving them into an expanded position. With the blades 205 in an expanded position, the surgeon can easily manipulate the now planar mesh patch 100 to position the mesh patch 100 over or behind the hernia defect. Additionally, the surgeon can pull the mesh patch 100 against a fascia wall and away from the viscera (other anatomical features or internal organs) to help prevent the unintentional puncture of the viscera when suturing the mesh patch 100 to the patient.

At block 625, once the mesh patch 100 is positioned, the surgeon then sutures the mesh patch 100 in place. For one embodiment, the surgeon sutures the top ply of the mesh patch 100 to anchor the mesh patch 100 to the hernia defect. Alternatively, the surgeon utilizes suture tabs 115 to affix the mesh patch 100. The expanded position and width of the blades 205 provide a barrier between the top ply of the mesh patch 100 to be sutured and viscera beneath the hernia defect. This barrier helps prevent the unintentional puncture of the viscera when suturing the mesh patch 100 to the patient.

At block 630, the surgeon uses the control 215 to move the blades 205 from the expanded position back to a clustered position. At block 635, the surgeon then removes the blades 205 from the mesh patch 100 (via the opening 110) and removes the placement tool 200 from the patient.

Alternatively to using the mesh patch 100 and placement tool 200 described above, the hernia defect may be repaired using a mesh patch including a non-permeable tunnel containing a viscous anti-bacterial gel. For one embodiment, the mesh patch (not shown) includes a tunnel that traverses the perimeter or near the perimeter of the mesh patch. For one embodiment, the tunnel would include a receptacle for a syringe for the insertion and removal of the viscous gel.

For one embodiment, when the tunnel is filled with a viscous gel, the mesh patch would be flexible—i.e., it could be compressed for insertion into a patient. The viscous gel would, when a compressing force is released, cause the mesh patch to expand in a planar fashion. Alternatively, the mesh patch would be compressed and inserted into the patient without the gel and the viscous gel would be added to the tunnel once the mesh patch is inside the patient to maintain the mesh patch in a planar shape.

Similar to the mesh patch 100 described above, one embodiment of the mesh patch utilizing viscous gel includes suture tabs for affixing the mesh patch to the patient. Once the planar mesh patch is positioned and affixed to a patient, the surgeon inserts a syringe and removes the viscous gel. The gel provides sufficient spring tension and memory to keep the mesh planar and, once the gel is removed, no unnecessary additional foreign material is left in the patient.

In the foregoing specification, the invention has been described with reference to specific exemplary embodiments thereof. It will be evident that various modifications may be made thereto without departing from the broader spirit and scope of the invention. Although for one embodiment of the invention the mesh patch is circular in shape, any shape or size mesh patch can be employed. Further, although one embodiment of the invention is used for repairing abdominal wall hernias, this invention may be applied to other hernia types. The specification and drawings are, accordingly, to be regarded in an illustrative sense rather than a restrictive sense.

What is claimed is:

1. A hernia mesh system comprising:
a mesh patch including a top ply and a bottom ply, wherein the top ply includes an opening; and
a placement tool including
an elongated handle having a proximal end and a distal end,
a plurality of rigid blades, each of the blades having a proximal end and a distal end, the proximal end of the blades coupled to the distal end of the elongated handle, and
a control to rotate the rigid blades around a longitudinal axis of the elongated handle in first and second directions, the rotation of the blades in the first direction causing each of one or more of the blades to pivot about the proximal end of the blade and distal end of the elongated handle, moving the plurality of blades from a clustered position in which the distal ends of the blades overlap one another or are positioned side-by-side, allowing the distal ends of the blades to be inserted in the opening in the mesh patch in the clustered position, to an expanded position in which the distal ends of the blades spread the mesh patch out in a planar fashion, and the rotation of the blades in the second direction causing the one or more of the blades to pivot about the proximal end of the blade and distal end of the elongated handle, moving the plurality of blades from the expanded position to the clustered position wherein the control is a dial near the proximal end of the placement tool and rotation of the dial causes rotation of the one or more of the plurality of blades in the first and second directions.

2. The system of claim 1, wherein the blades are substantially perpendicular to the elongated handle in the expanded position.

3. The system of claim 2, wherein the blades are moveable from a position that is substantially parallel with the elongated handle to a position that is substantially perpendicular to the elongated handle.

4. The system of claim 1, further comprising:
a dissolvable suture tab affixed to the mesh patch.

5. The system of claim 1, wherein the opening in the mesh patch is reinforced around a perimeter of the opening.

6. The system of claim 1, wherein the placement tool is comprised of a reusable material that can withstand heated sterilization.

7. The system of claim 1, wherein a first of the plurality of blades includes a slot to receive a raised feature from a second of the plurality of blades, wherein the slot provides a limited path for the raised feature to travel as the second blade rotates, and wherein rotation of the second blade causes the first blade to rotate when the raised feature reaches an end of the limited path of the slot.

8. A surgical apparatus to place a mesh patch within a patient, the apparatus comprising:
an elongated handle having a proximal end and a distal end;
a plurality of rigid blades, each of the blades having a proximal end and a distal end, the proximal end of the blades coupled to the distal end of the elongated handle; and
a control to rotate the rigid blades around a longitudinal axis of the elongated handle in first and second directions, the rotation of the blades in the first direction causing each of one or more of the blades to pivot about the proximal ends of the blade and distal end of the elongated handle, moving the plurality of blades from a clustered position in which the distal end of the blades overlap one another or are positioned side-by-side, allowing the distal ends of the blades to be inserted in an opening in the mesh patch in the clustered position, to an expanded position in which the distal ends of the blades spread the mesh patch out in a planar fashion, and the rotation of the blades in the second direction causing the one or more of the blades to pivot about the proximal end of the blade and distal end of the elongated handle, moving the plurality of blades from the expanded position to the clustered position wherein the control is a dial near the proximal end of the elongated handle and rotation of the dial causes rotation of the one or more of the plurality of blades in the first and second directions.

9. The apparatus of claim 8, wherein the blades are substantially perpendicular to the elongated handle in the expanded position.

10. The apparatus of claim 8, wherein the blades are moveable from a position that is substantially parallel with the elongated handle to a position that is substantially perpendicular to the elongated handle.

11. The apparatus of claim 8, wherein the elongated handle, plurality of blades, and control are comprised of a reusable material that can withstand heated sterilization.

12. The apparatus of claim 8, wherein a first of the plurality of blades includes a slot to receive a raised feature from a second of the plurality of blades, wherein the slot provides a limited path for the raised feature to travel as the second blade rotates, and wherein rotation of the second blade causes the first blade to rotate when the raised feature reaches an end of the limited path of the slot.

* * * * *